(12) United States Patent
Keem (10) Patent No.: US 11,559,410 B2
(45) Date of Patent: Jan. 24, 2023

(54) ARTIFICIAL SPINAL DISC AND ARTIFICIAL DISC INSERTION METHOD USING THE SAME

(71) Applicant: HILO INNOVATIONS, LLC, Mercer Island, WA (US)

(72) Inventor: Sean Kyong-Ho Keem, Mercer Island, WA (US)

(73) Assignee: HILO INNOVATIONS, LLC, Mercer Island, WA (US)

( * ) Notice: Subject to any disclaimer, the term of this patent is extended or adjusted under 35 U.S.C. 154(b) by 0 days.

(21) Appl. No.: 17/424,883

(22) PCT Filed: Feb. 5, 2021

(86) PCT No.: PCT/IB2021/050930
§ 371 (c)(1),
(2) Date: Jul. 21, 2021

(87) PCT Pub. No.: WO2020/161647
PCT Pub. Date: Aug. 13, 2020

(65) Prior Publication Data
US 2022/0151799 A1      May 19, 2022

(51) Int. Cl.
*A61F 2/44* (2006.01)
*A61F 2/30* (2006.01)

(52) U.S. Cl.
CPC .. *A61F 2/4425* (2013.01); *A61F 2002/30156* (2013.01); *A61F 2002/30245* (2013.01); *A61F 2002/30253* (2013.01); *A61F 2002/30649* (2013.01)

(58) Field of Classification Search
CPC .............. A61F 2/4425; A61F 2002/443; A61F 2002/30649; A61F 2002/30253; A61F 2002/30245; A61F 2002/30156
See application file for complete search history.

(56) References Cited

U.S. PATENT DOCUMENTS

| | | | | |
|---|---|---|---|---|
| 5,425,773 | A | * | 6/1995 | Boyd .................... A61F 2/4425 623/17.15 |
| 7,806,933 | B2 | | 10/2010 | Sears et al. |
| 2007/0198089 | A1 | | 8/2007 | Moskowitz et al. |
| 2007/0233262 | A1 | * | 10/2007 | Amin ................... A61F 2/4425 623/17.15 |

(Continued)

FOREIGN PATENT DOCUMENTS

| KR | 10-2009-9008409 A | 1/2009 |
|---|---|---|
| KR | 10-2010-0032868 A | 3/2010 |

(Continued)

*Primary Examiner* — Christopher D. Prone
(74) *Attorney, Agent, or Firm* — Bridgeway IP Law Group, PLLC; Sang Ho Lee; Hyun Woo Shin (57) ABSTRACT

Provided is an artificial spinal disc including an upper disc formed in a plate shape with top coupled to an upper vertebra, a protruding joint portion protruding from a lower surface of the upper disc, and a lower disc formed in a plate shape with bottom coupled to a lower vertebra wherein the protruding joint portion is seated on an upper surface of the lower disc. According to the foregoing description, the artificial disc is implanted through the lateral or anterolateral approach to the spine, rather than the anterior approach, and such lateral implantation is straightforward.

18 Claims, 8 Drawing Sheets

(56) References Cited

U.S. PATENT DOCUMENTS

| | | |
|---|---|---|
| 2008/0195212 A1 | 8/2008 | Nguyen et al. |
| 2008/0300685 A1 | 12/2008 | Carls et al. |
| 2018/0049887 A1 | 2/2018 | Nguyen et al. |

FOREIGN PATENT DOCUMENTS

| | | |
|---|---|---|
| KR | 10-1410181 B1 | 6/2014 |
| KR | 10-1964862 B1 | 4/2019 |

* cited by examiner

ARTIFICIAL SPINAL DISC AND ARTIFICIAL DISC INSERTION METHOD USING THE SAME

TECHNICAL FIELD

The present disclosure relates to an artificial spinal disc and an artificial disc insertion method using the same, and more particularly, to an artificial spinal disc which is used to replace a damaged disc in the spine for the treatment of a spinal disc related disease and an artificial disc insertion method for inserting an artificial disc into the spine.

BACKGROUND ART

In general, discs serve as cushions between vertebrae to absorb loads and impacts of the body applied to the spinal column. Discs distribute impacts like springs, hold the vertebrae not to move out of place, separate two vertebrae to prevent nerve compression in the neuroforamina in motion, and help each vertebra to move smoothly.

Meanwhile, since discs frequently absorb and transmit vertically applied loads and impacts, a variety of diseases associated with disc trauma can occur, such as spinal stenosis, osteophyte formation, disc herniation, and nerve root compression. One treatment method for diseases associated with discs involves removal of a damaged intervertebral disc, and implanting an artificial disc in the space between two adjacent vertebrae to restore the function of the spine.

The artificial disc generally should have a proper thickness and anatomic restoration to restore the original height of the intervertebral disc.

Meanwhile, as an example of a conventional artificial disc, Korean Patent No. 10-1964862 discloses an artificial disc for cervical spine including an upper plate, a lower plate and an elastic member, a first groove formed in the shape of a dome on the bottom of the upper plate to receive the top of the elastic member, a circular second groove formed on the upper surface of the lower plate to receive the bottom of the elastic member, a concave portion formed in the shape of a dome recessed downward from the second groove of the lower plate to prevent contact with the bottom of the elastic member, a plurality of upper slots formed on the upper surface of the upper plate in the horizontal direction to prevent anterior movement of the artificial disc, and a plurality of lower slots formed on the bottom of the lower plate in the horizontal direction to prevent anterior movement of the artificial disc.

However, the conventional artificial discs require an intricate manufacturing process due to their complex shapes, and often fail to effectively ensure spinal mobility after surgery.

Additionally, the conventional artificial discs are implanted by the anterior approach to the spine through the abdomen, and since the anterior approach involves abdominal insertion and implantation, the artificial disc passes through the main arteries and the main veins. Thus, there is an increased risk of damage to the major blood vessels during surgery. Furthermore, the implantable artificial disc may migrate forward, causing a serious danger to the vital structures near the spine.

RELATED LITERATURES

Patent Literatures

Korean Patent No. 10-1964862

DISCLOSURE

Technical Problem

The present disclosure is directed to providing an artificial spinal disc which has a simple shape, is easy to manufacture, improves spinal mobility for a patient with a damaged disc and ensures stability after surgery, and an artificial disc insertion method using the same.

The present disclosure is further directed to providing an artificial spinal disc which is implanted by the lateral or anterolateral approach to the spine, not the anterior approach, and has an optimal shape for effective lateral implantation to reduce the risk of damage to the major vessels or other vital organs, which may be caused by surgery using the anterior approach, and an artificial disc insertion method using the same.

Technical Solution

The present disclosure provides an artificial spinal disc inserted between an upper vertebra and a lower vertebra, the artificial spinal disc including an upper disc formed in a plate shape, with top coupled to the upper vertebra, a protruding joint portion including a main joint portion protruding from a lower surface of the upper disc, and one or multiple auxiliary joint portions spaced apart from a side of the main joint portion and protruding from the lower surface of the upper disc, and a lower disc formed in a plate shape, with bottom coupled to the lower vertebra, the lower disc having, on an upper surface, a main joint groove in which the main joint portion is seated and an auxiliary joint groove in which the auxiliary joint portion is seated to allow the protruding joint portion to make multidirectional movements.

Here, the auxiliary joint portion may include a first auxiliary joint portion disposed at a distance on one horizontal side of the main joint portion, and a second auxiliary joint portion disposed at a distance on the other horizontal side of the main joint portion.

Preferably, the first auxiliary joint portion and the second auxiliary joint portion are symmetrically disposed with respect to the main joint portion on a plane.

Each of the first auxiliary joint portion and the second auxiliary joint portion may be formed in a hemispherical shape.

Alternatively, each of the first auxiliary joint portion and the second auxiliary joint portion may be formed in a semi-ellipsoidal shape. In this case, each of the first auxiliary joint portion and the second auxiliary joint portion may be formed such that a long axis connecting two points on a plane is disposed along a front-rear direction of a spine.

The main joint portion may be formed in a hemispherical shape.

Alternatively, the main joint portion may be formed in a semi-ellipsoidal shape. In this case, the main joint portion may be formed such that a long axis connecting two points on a plane is disposed along a left-right direction of a spine.

The main joint portion may protrude higher than a protrusion height of the auxiliary joint portion.

Further, the protruding joint portion may be integrally formed with the upper disc.

Preferably, the upper disc and the lower disc are spaced apart from each other at a distance between the lower surface of the upper disc and the upper surface of the lower disc in a range of 3 mm to 6 mm when the protruding joint portion is seated.

Preferably, the first auxiliary joint portion and the second auxiliary joint portion are formed with a smaller planar area than a planar area of the main joint portion.

The auxiliary joint portion may be formed such that a center of each of the first auxiliary joint portion and the second auxiliary joint portion is disposed at an anterior portion of a spine with respect to a center of the main joint portion on a plane.

The first auxiliary joint portion and the second auxiliary joint portion may be configured to have a same shape and planar area.

The upper disc and the lower disc may include a first side formed along one anterior side of the main joint portion and one anterior side of the first auxiliary joint portion, a second side having one side connected to one side of the first side and formed along the other anterior side of the main joint portion and one anterior side of the second auxiliary joint portion to form a set angle with the first side, and a third side having one side connected to the other side of the first side and the other side connected to the other side of the second side and formed along one posterior side of the first auxiliary joint portion and one posterior side of the second auxiliary joint portion.

The upper disc and the lower disc may have a plane shape of an approximate triangular shape formed by the first side, the second side and the third side.

Meanwhile, the upper disc and the lower disc may be formed in the shape of an isosceles triangle such that two insertion sides of the first auxiliary joint portion or the second auxiliary joint portion are narrow and the third side is long in the horizontal direction, when inserted through the lateral or anterolateral approach to the spine. In this instance, an angle between the first side and the second side with respect to the third side may be 18° to 22°, or an internal angle of intersection between a first imaginary line connecting the center of each of the first auxiliary joint portion and the second auxiliary joint portion and a second imaginary line connecting the center of each of the main joint portion, the first auxiliary joint portion and the second auxiliary joint portion may be 18° to 22°.

Each of the upper disc and the lower disc may be arranged with the third side facing an anterior side of a spine.

Each of the upper disc and the lower disc may be configured to have one or multiple concave portions on the third side.

The upper disc and the lower disc may include a first curved side formed along an anterior side of each of the first auxiliary joint portion, the main joint portion and the second auxiliary joint portion, and curved concavely on a plane, and a second curved side connected to the first curved side, formed along a posterior side of each of the first auxiliary joint portion, the main joint portion and the second auxiliary joint portion and curved convexly on the plane.

According to another aspect of the present disclosure, the present disclosure provides an artificial disc insertion method including inserting an artificial disc into an implantation space between an upper vertebra and a lower vertebra of a human body, the artificial disc including an upper disc formed in a plate shape, with top coupled to the upper vertebra, a protruding joint portion including a main joint portion protruding from a lower surface of the upper disc and one or multiple auxiliary joint portions spaced apart from a side of the main joint portion and protruding the lower surface of the upper disc, and a lower disc formed in a plate shape, with bottom coupled to the lower vertebra, the lower disc having, on an upper surface, a main joint groove in which the main joint portion is seated and an auxiliary joint groove in which the auxiliary joint portion is seated to allow the protruding joint portion to make multidirectional movements, wherein the artificial disc is inserted through a lateral or anterolateral approach to a spine and the auxiliary joint portion is first inserted into the implantation space, pushing the artificial disc into the implantation space such that the main joint portion is disposed at a center of the upper vertebra and the lower vertebra on a plane, and adjusting a location of the artificial disc.

Advantageous Effects

The artificial spinal disc according to the present disclosure and the artificial disc insertion method using the same may provide the following effects.

First, the artificial spinal disc according to the present disclosure is easy to manufacture due to its simple shape, and it is possible to improve the spinal mobility and ensure stability after surgery.

Second, it is possible to perform safer surgery without any risk of damage to blood vessels or other organs that may occur due to surgery using the anterior approach. This advantage is achieved by implanting the artificial disc with either the lateral or anterolateral approach to the spine, rather than the anterior approach, to avoid risking the vital structures in the human body, and by optimizing the shapes of the upper disc and the lower disc to make lateral or anterolateral implantation easier.

Third, the artificial spinal disc according to the present disclosure allows for broader and more free movements, as the location of the center of rotation and the slope of the spine through the main joint portion and the auxiliary joint portion are configured to closely mimic natural movements of the spine to the greatest extent, thereby preventing stress and fatigue with the surrounding tissues and improving a patient's joint mobility.

Fourth, the protruding joint portion includes the main joint portion as well as two auxiliary joint portions to increase the contact surface of the joint within the artificial disc, thereby greatly increasing the stability of spinal mobilization after surgery. Additionally, since the increased contact surface through the main joint portion and the two auxiliary joint portions ensures stability, it is possible to resolve issues concerning the reduced area of the center of rotation that may be involved in the lateral or anterolateral approach.

BEST MODE

Hereinafter, the preferred embodiments of the present disclosure will be described in detail with reference to the accompanying drawings.

Figure 1:
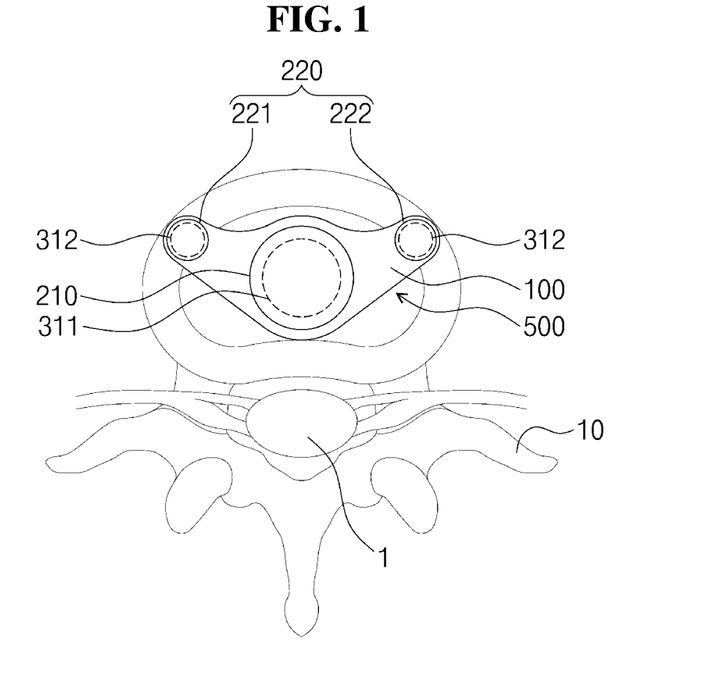
FIG. 1 is a plan view showing an artificial spinal disc according to an embodiment of the present disclosure inserted into the spine.

First, the present disclosure is inserted and implanted into an implantation space between an upper vertebra and a lower vertebra in place of a damaged disc after the damaged disc is removed, and FIG. 1 is a plan view showing an artificial spinal disc 500 according to an embodiment of the present disclosure (hereinafter referred to as an 'artificial disc') implanted into the spine. In the drawing, the reference number 1 indicates the spinal cord, and the reference number 10 indicates the transverse process of the vertebra.

Figure 2:
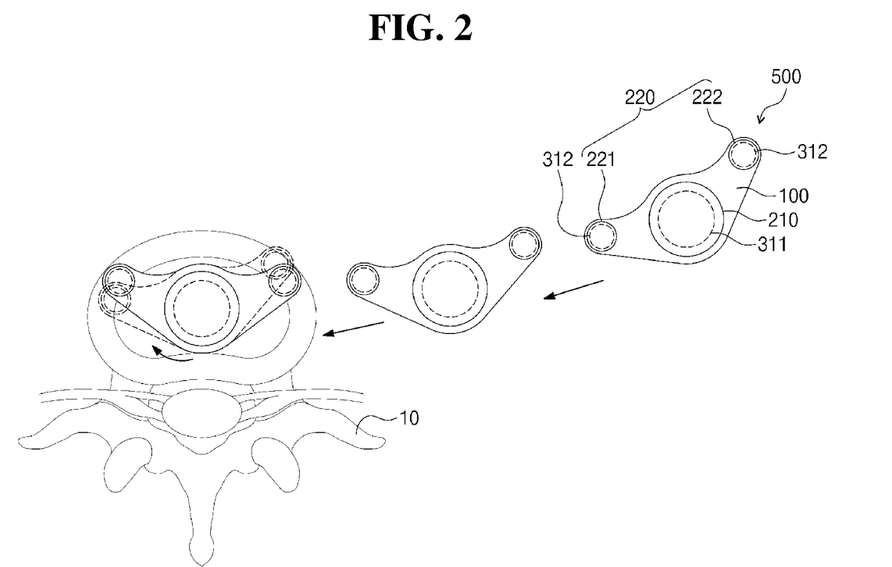
FIG. 2 is a plan view showing an artificial spinal disc insertion method according to an embodiment of the present disclosure.

Meanwhile, as shown in FIG. 2, an artificial disc insertion method according to an embodiment of the present disclosure inserts the artificial disc 500 into the implantation space between the upper vertebra and the lower vertebra through the lateral or anterolateral approach to the spine, and as opposed to the conventional anterior approach of inserting the artificial disc 500 from the anterior of the spine, this approach avoids the major organs, blood vessels and so on, thereby minimizing the risk of injury associated with artificial disc replacement surgery.

Additionally, since the artificial disc 500 of the present disclosure is inserted through the lateral or anterolateral approach to the human body as opposed to the conventional anterior approach, when considering this, the artificial disc 500 may be formed in an anatomically optimal shape to ease the insertion and implantation through the lateral or anterolateral approach to the spine and minimize tissue damage.

Prior to description of the artificial disc 500, the method for inserting the artificial spinal disc will be described with reference to FIG. 2.

First, the artificial disc 500 is coupled to an insertion instrument (not shown) and inserted into the implantation space between the upper vertebra and the lower vertebra in the human body through the insertion instrument to a set location on the lateral or anterolateral position of the spine.

Describing the artificial disc insertion method in detail, first, the narrow side of the artificial disc 500 in which a first auxiliary joint portion 221 or a second auxiliary joint portion 222 is disposed as described below is inserted into the implantation space. In this instance, since the artificial disc 500 has two narrow sides and a wide center, the side of the artificial disc 500 formed in a narrow shape for an easy entry into the tissue in the human body is first inserted, in which the first auxiliary joint portion 221 or the second auxiliary joint portion 222 is disposed.

When the first auxiliary joint portion 221 or the second auxiliary joint portion 222 is first inserted, the artificial disc 500 is pushed into the implantation space to place a main joint portion 210 and the second auxiliary joint portion 222 or the first auxiliary joint portion 221 in the implantation space. In this instance, the main joint portion 210 may be disposed at the center of the upper vertebra and the lower vertebra on the plane in the implantation space, and this is a location taking the movement of the spine into account, and the location may be changed depending on the shape of the corresponding spine.

Meanwhile, since the artificial disc 500 is inserted by the lateral or anterolateral approach to the spine, when the artificial disc 500 is inserted into in the implantation space, the first auxiliary joint portion 221 and the second auxiliary joint portion 222 are not disposed on the same horizontal line and they are slanted at a set angle. Thus, when the insertion of the artificial disc 500 is completed, it is necessary to adjust the location of the artificial disc 500.

Accordingly, the method ends with adjusting the location of the artificial disc 500 by axially rotating the artificial disc 500 so that the first auxiliary joint portion 221 and the second auxiliary joint portion 222 are disposed on the same horizontal line facing the anterior side of the spine, with the main joint portion 210 disposed at the installation location, i.e., at the center of the upper vertebra and the lower vertebra on the plane, as shown.

According to the foregoing description, due to the insertion through the lateral or anterolateral approach to the spine, the artificial disc insertion method of the present disclosure avoids the major organs, the main arteries, the main veins and so on, thereby preventing damage to the human body that may occur during the surgery, and reducing unnecessary dissection, which facilitates post-operative recovery. Additionally, due to the insertion through the lateral or anterolateral approach to the spine, the artificial disc insertion method of the present disclosure can preserve the anterior longitudinal ligament (ALL) in the insertion process, thereby avoiding potentially devastating complications that may occur with anterior extrusion of the artificial disc.

Meanwhile, since it is inserted through the lateral approach to the spine, not the anterior approach, the artificial disc 500 is formed with a small width and a large horizontal length for easy lateral insertion, and configured to be inserted using the narrow side as an insertion end.

In other words, the artificial disc 500 is formed in an optimal shape for easy lateral insertion into the spine, and hereinafter the details including the shape of the artificial disc 500 will be described.

Figure 3:
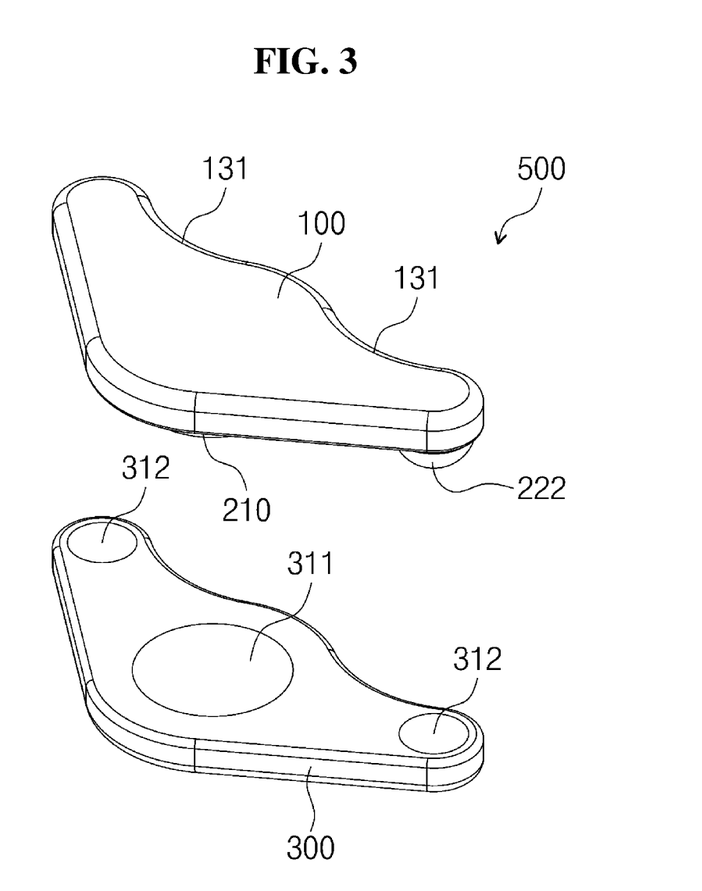
FIG. 3 is an exploded perspective view of an artificial spinal disc according to an embodiment of the present disclosure.

Referring to FIG. 3, the artificial spinal disc 500 according to an embodiment of the present disclosure is inserted into the implantation space between the upper vertebra and the lower vertebra adjacent to each other, and may include an upper disc 100, a protruding joint portion 200 and a lower disc 300.

First, the upper disc 100 is formed in the shape of a plate having a set thickness, and is coupled and fixed to the bottom of the upper vertebra in the implantation space from which the disc has been removed. Although the drawing shows the upper disc 100 formed with an equal width (height), this is an example and the upper disc 100 may be formed with a tapered thickness or varying thickness of each location depending on the shape of the implantation space or the shape of the upper vertebra.

Although not shown, the upper disc 100 may be fixed with the upper vertebra through a fixing means. Here, for fixing with the upper vertebra, the fixing means may include a wedge type fixing protrusion (spike) protruding from the upper surface of the upper disc 100, a porous surface to facilitate the bone growth or a fixing pin, and a variety of other configurations for fixing with the upper vertebra may be applied. The fixing means may be integrally formed with the upper disc 100 into a product in the manufacture of the upper disc 100.

The plane of the upper disc 100 may have an approximate triangular shape as shown, to facilitate the lateral insertion into the spine. However, this is an example, and the upper disc 100 may be formed in various shapes including a streamlined or kidney bean shape, and various embodiments of the upper disc 100 will be described in FIGS. 9, 10 and 12 below.

Meanwhile, when the upper disc 100 is formed in the shape of a triangle having a first side 110, a second side 120 and a third side 130 on the plane, a concave portion 131 may be formed on the third side 130 as shown. To contribute to the material reduction and facilitate the insertion, the concave portion 131 may be formed in various shapes.

Figure 4:
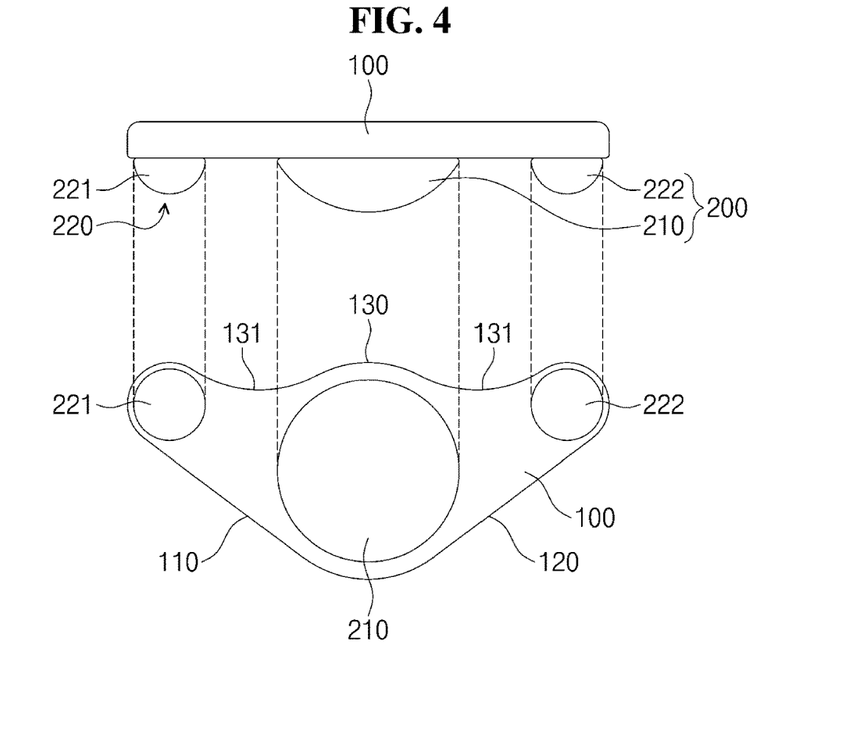
FIG. 4 is plan and front views showing an upper disc of an artificial spinal disc according to an embodiment of the present disclosure.

Referring to FIG. 4, the protruding joint portion 200 plays a role in allowing the upper disc 100 and the lower disc 300 to make multidirectional free movements, and through this, closely mimicking natural movements of the spine.

The protruding joint portion 200 protrudes downward from the lower surface of the upper disc 100 and comes into contact with the upper surface of the lower disc 300.

The protruding joint portion 200 may be integrally formed with the upper disc 100 using the same material.

As shown in FIG. 4, the protruding joint portion 200 may include the main joint portion 210 and one or multiple auxiliary joint portions 220.

The main joint portion 210 may be disposed at a location at which joint movements of the spine are made or at the center of the vertebrae on the plane after the implantation of the artificial disc 500.

The main joint portion 210 may be formed in a hemispherical or semi-ellipsoidal shape according to the settings of the range of rotation and the center of mass.

Meanwhile, when the shape of the main joint portion (210a in FIGS. 11, 12 and 13) is a semi-ellipsoidal shape, the main joint portion 210a is preferably formed such that the long axis connecting two points on the plane is disposed along the left-right direction of the spine. In general, the spine has a larger range of forward-backward movement (extension, flexion) than the range of leftward-rightward movement (lateral bending), and considering this, the long axis is disposed along the left-right direction of the spine to further increase the range of forward-backward movement.

Figure 6:
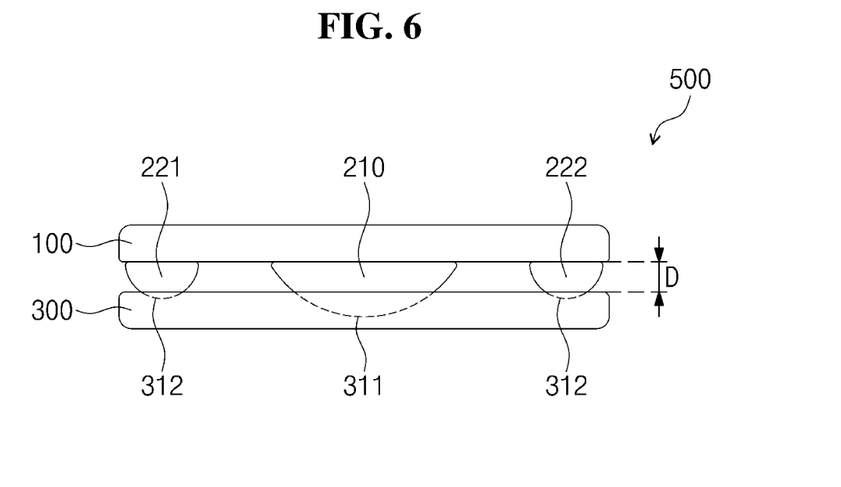
FIG. 6 is a front view of an artificial spinal disc according to an embodiment of the present disclosure.

The main joint portion 210,210a preferably protrudes to a larger height than the protrusion height of the auxiliary joint portion 220 (see FIG. 6). The main joint portion 210,210a responsible for main joint movements has a large protrusion height for effective multidirectional movements.

The auxiliary joint portion 220 plays a role in maintaining the coronal and sagittal balance of the artificial disc 500, and complements and supports the main joint portion 210,210a that inevitably has a smaller size than the joint of the conventional artificial disc due to the insertion through the lateral or anterolateral approach.

The auxiliary joint portion 220 is spaced apart from the side of the main joint portion 210, and protrudes from the lower surface of the upper disc 100. In the same way as the above-described main joint portion 210, the auxiliary joint portion 220 may be integrally formed with the upper disc 100 using the same material.

Referring to FIG. 4, a pair of auxiliary joint portions 220 may be each disposed on two sides of the main joint portion 210, spaced apart from each other, and may include the first auxiliary joint portion 221 and the second auxiliary joint portion 222.

The first auxiliary joint portion 221 is disposed at a distance on one horizontal side of the main joint portion 210. Additionally, the second auxiliary joint portion 222 is disposed at a distance on the other horizontal side of the main joint portion 210.

Here, the first auxiliary joint portion 221 and the second auxiliary joint portion 222 may be configured with the same shape and planar area.

Additionally, each of the first auxiliary joint portion 221 and the second auxiliary joint portion 222 may be disposed symmetrically in the horizontal direction with respect to the main joint portion 210 on the plane. In detail, each of the first auxiliary joint portion 221 and the second auxiliary joint portion 222 is configured such that its center is disposed at the anterior portion of the spine with respect to the center of the main joint portion 210 on the plane.

Additionally, the first auxiliary joint portion 221 and the second auxiliary joint portion 222 may be formed with a smaller planar area than the planar area of the main joint portion 210.

Here, the main joint portion 210, the first auxiliary joint portion 221 and the second auxiliary joint portion 222 are preferably arranged in the shape of an isosceles triangle having a long base by connecting the center of each of the main joint portion 210, the first auxiliary joint portion 221 and the second auxiliary joint portion 222 on the plane. In this instance, each of the main joint portion 210, the first auxiliary joint portion 221 and the second auxiliary joint portion 222 is disposed adjacent to each vertex location of the triangular shape on the plane, and in this state, the base corresponds to a line connecting the center of each of the first auxiliary joint portion 221 and the second auxiliary joint portion 222.

Meanwhile, referring to FIG. 4, the upper disc 100 has the plane shape which is narrow on two sides and long in the horizontal direction on the whole, to ease the lateral insertion into the spine, and this shape facilitates the lateral insertion into the spine. In other words, the upper disc 100 may be formed in the shape of an isosceles triangle having the long third side 130 in the horizontal direction and two insertion sides of the first auxiliary joint portion 221 or the second auxiliary joint portion 222 which are narrow when inserted in the lateral direction of the spine.

In detail, when it is assumed that the main joint portion 210 and the pair of auxiliary joint portions 220 are arranged in a triangular shape, an internal angle between two sides (the first side 110 and the second side 120) with respect to the base (the third side 130) of the triangle is preferably 18° to 22°. Alternatively, an internal angle of intersection between a first imaginary line connecting the center of each of the first auxiliary joint portion 221 and the second auxiliary joint portion 222 and a second imaginary line connecting the center of each of the main joint portion 210, the first auxiliary joint portion 221 and the second auxiliary joint portion 222 is preferably 18° to 22°.

When the angle is less than 18°, the shape of the upper disc 100 increases in the horizontal direction, and a space for formation of the main joint portion 210 reduces, resulting in reduced range of motion of the artificial disc 500. In contrast, when the angle is higher than 22°, the central width of the upper disc 100 increases and the lateral insertion into the spine may not be easy.

The auxiliary joint portion 220 may be formed in a hemispherical or semi-ellipsoidal shape. In this instance, when the auxiliary joint portion 220 is a semi-ellipsoidal shape, the auxiliary joint portion 220 is preferably formed such that the long axis connecting two points on the plane is disposed along the front-rear direction of the spine (see FIG. 8).

Further, the main joint portion 210 may be spaced apart in the other direction with respect to one directional same tangent line of the first auxiliary joint portion 221 and the second auxiliary joint portion 222 on the plane, such that the upper side of the main joint portion 210 may be disposed at the lower position than the upper side of the first auxiliary joint portion 221 and the second auxiliary joint portion 222 on the plane.

Figure 5:
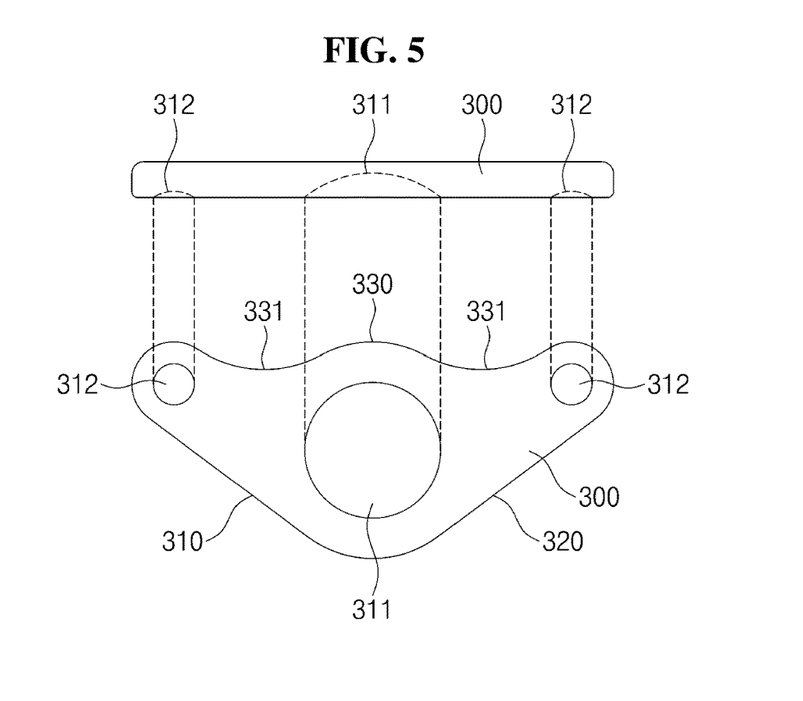
FIG. 5 is plan and front views showing a lower disc of an artificial spinal disc according to an embodiment of the present disclosure.

Referring to FIG. 5, the lower disc 300 is disposed at a distance below the upper disc 100, formed in the shape of a plate having a set thickness, and coupled and fixed onto the lower vertebra of the implantation space.

The lower disc 300 may be formed with the same width (height) and plane shape to match the upper disc 100, and may be fixed with the lower vertebra through the above-described fixing means. In the drawing, the lower disc 300 may be formed in an approximate triangular shape having a first side 310, a second side 320 and a third side 330 to match the plane shape of the upper disc 100, and in the same way as the upper disc 100, a concave portion 331 may be formed on the third side 330 as shown.

The lower disc 300 may have, on the upper surface, a joint groove in which the protruding joint portion 200 is seated to allow multidirectional movements. The joint groove may be configured to provide translational and rotational movements of the spine such as flexion, extension, side bending, and axial rotation (twisting), while maintaining slidable contact with the side of the protruding joint portion 200.

The joint groove may include a main joint groove 311 in which the main joint portion 210 is seated, and an auxiliary joint groove 312 in which the auxiliary joint portion 220 is seated. Here, the main joint groove 311 may be formed in the same hemispherical or semi-ellipsoidal shape to match the shape of the main joint portion 210, and the auxiliary joint groove 312 may be formed in the same hemispherical or semi-ellipsoidal shape to match the shape of the auxiliary joint portion 220, to bring that the main joint portion 210 and the auxiliary joint portion 220 into contact with the main joint groove 311 and the auxiliary joint groove 312.

Figure 14:
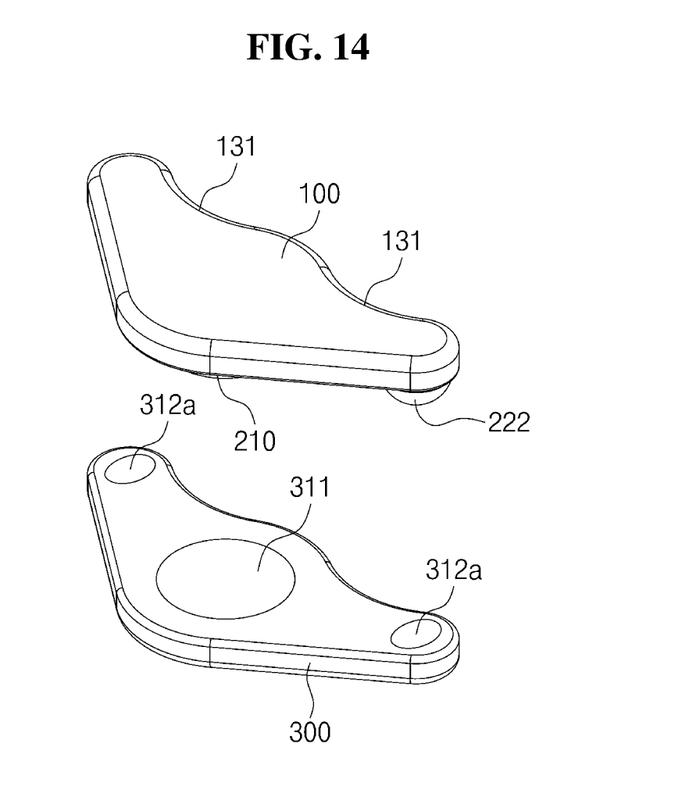
FIG. 14 is a perspective view showing another embodiment of an auxiliary joint portion of an upper disc and an auxiliary joint groove of a lower disc in an artificial spinal disc according to an embodiment of the present disclosure.

Meanwhile, an auxiliary joint groove 312*a* may be formed in a different shape from the corresponding auxiliary joint portion 220, not in the same shape (see FIG. 14). The auxiliary joint portion 220 may be formed in a hemispherical shape and the corresponding auxiliary joint groove 312*a* may be formed in a semi-ellipsoidal shape, and its detailed description will be provided in FIG. 14 below.

The upper disc 100, the lower disc 300 and the protruding joint portion 200 may be formed from metals such as titanium or carbon alloys or ceramics which are harmless to the human body and can withstand impacts and loads applied to the spine for a long time, but a variety of materials for achieving the above-described object may be applied.

Figure 7:
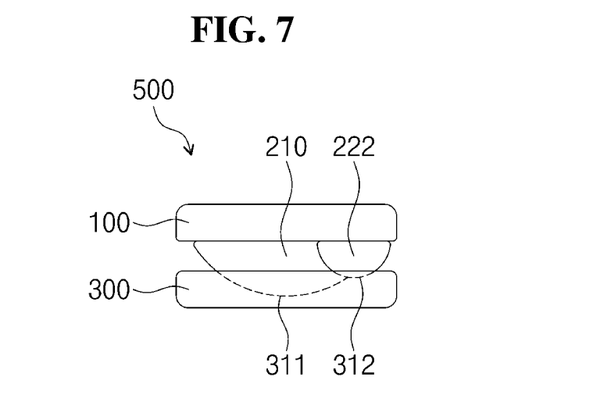
FIG. 7 is a side view of an artificial spinal disc according to an embodiment of the present disclosure.

Referring to FIGS. 6 and 7, when the protruding joint portion 200 is seated, the upper disc 100 and the lower disc 300 are spaced a set distance D apart from each other to allow the joint portion to move. The distance is a factor that affects the range of motion of the artificial disc 500, and with the increasing distance, the thickness of the upper disc 100 and the lower disc 300 reduces and the stability reduces, and with the decreasing distance, the range of motion reduces.

Accordingly, the artificial disc 500 preferably has the vertical distance between the lower surface of the upper disc 100 and the upper surface of the lower disc 300 in the range of 3 mm to 6 mm. As described above, when the distance is less than 3 mm, the side of the upper disc 100 and the side of the lower disc 300 interfere with each other during motion, which affects the motion of the artificial disc 500, resulting in reduced range of motion. When the distance is more than 6 mm, since the total height from the upper surface of the upper disc 100 to the lower surface of the lower disc 300 is limited to a normal adult's disc insertion space (height), with the increasing distance between the upper disc 100 and the lower disc 300, the height (thickness) of the upper disc 100 and the lower disc 300 reduces, causing a problem with durability and stable support.

Hereinafter, various embodiments of the upper disc 100, the lower disc 300 and the protruding joint portion 200 will be described. Prior to description, since the upper disc 100, the lower disc 300 and the protruding joint portion 200 have been hereinabove described in detail, the detailed description is omitted herein, and the shape and location of each element will be described in detail.

Figure 8:
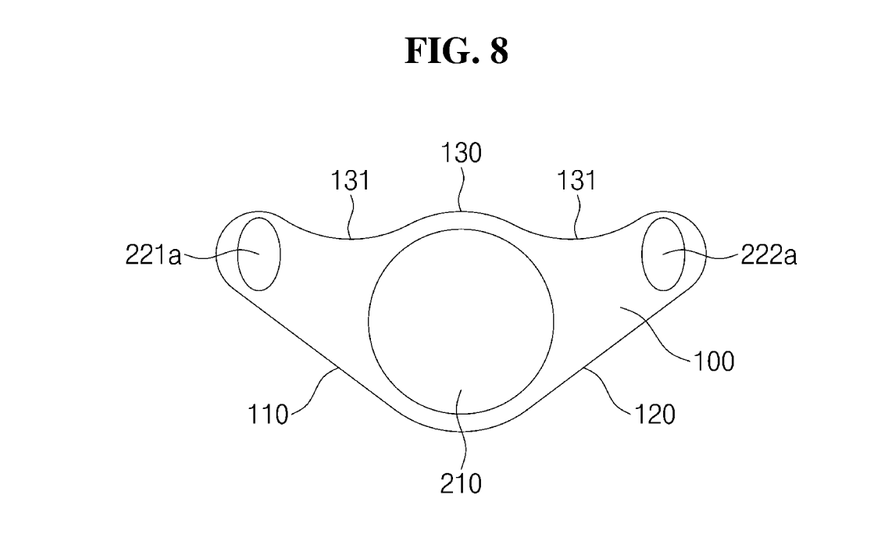
FIG. 8 is a plan view showing another embodiment of an auxiliary joint portion of an artificial spinal disc according to an embodiment of the present disclosure.

In a first embodiment, referring to FIG. 8, the plane shape of the upper disc 100 (the lower disc) has an approximate isosceles triangle shape.

In detail, the upper disc 100 and the lower disc 300 may have the plane shape of a triangular shape including the first side 110, the second side 120 and the third side 130.

The first side 110 is connected to one anterior side of the main joint portion 210 and one anterior side of the first auxiliary joint portion 221 with respect to the main joint portion 210.

The second side 120 has one side connected to one side of the first side 110 to form a set angle with the first side 110, and is connected to the other anterior side of the main joint portion 210 and one anterior side of the second auxiliary joint portion 222. In this instance, the first side 110 and the second side 120 correspond to two sides of the triangle except the base.

The third side 130 has one side connected to the other end of the first side 110 and the other side connected to the other side of the second side 120, is connected to one posterior side of the first auxiliary joint portion 221 and one posterior side of the second auxiliary joint portion 222, and corresponds to the base of the triangle.

As such, the upper disc 100 and the lower disc 300 may be formed in an approximate triangular shape on the plane by the first side 110, the second side 120 and the third side 130.

Meanwhile, first, each of the upper disc 100 and the lower disc 300 is preferably positioned such that the third side 130 faces the anterior side of the spine, considering the insertion direction (see FIG. 1).

In FIG. 8, the main joint portion 210 may be formed in a hemispherical shape, and the first auxiliary joint portion 221a and the second auxiliary joint portion 222a may be formed in a semi-ellipsoidal shape. In this instance, the auxiliary joint portion 220 is positioned in the up-down direction such that the long axis of the semi-ellipsoid faces the front-rear direction.

Additionally, the main joint portion 210 may be configured such that the horizontal tangent line to the uppermost surface is spaced apart in more downward direction than the uppermost horizontal tangent line of the auxiliary joint portion 220 so that the third side 130 may be concave.

Further, each of the upper disc 100 and the lower disc 300 may be configured to have one or multiple concave portions 131 on the third side 130. The concave portion 131 may reduce unnecessary material consumption of the upper disc 100 and the lower disc 300, and make the central width narrower so that the upper disc 100 and the lower disc 300 have a longer and thinner shape. Although the drawing shows two concave portions 131 each formed on two sides with respect to the main joint portion 210, this is an example and the number and locations may change.

Figure 9:
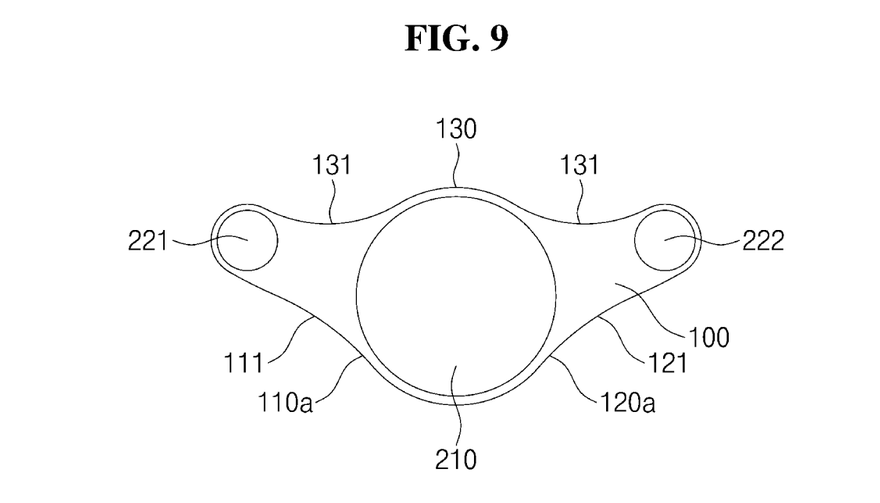
FIG. 9 is a plan view showing another embodiment of concave portions formed on the sides of an upper disc and a lower disc of an artificial spinal disc according to an embodiment of the present disclosure.

Meanwhile, in addition to the third side 130, the concave portions 111,121 may be respectively formed on a first side 110a and a second side 120a as shown in FIG. 9.

Figure 10:
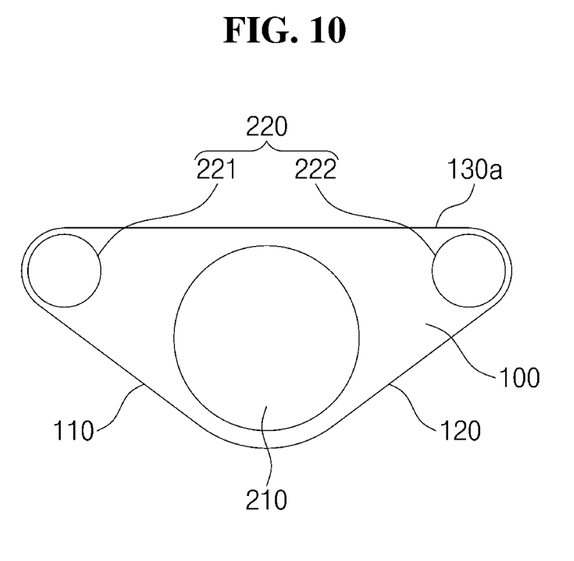
FIG. 10 is a plan view showing another embodiment of an upper disc and a lower disc of an artificial spinal disc according to an embodiment of the present disclosure.

In a second embodiment, referring to FIG. 10, the upper disc 100 and the lower disc 300 have a third side 130a formed in a flat shape, and the main joint portion 210 and the auxiliary joint portion 220 are formed in a hemispherical shape. In this case, the artificial disc 500 is easy to form the shape, and has increased contact area of the upper disc 100 and the lower disc 300 with the upper vertebra and the lower vertebra, respectively, thereby achieving more stable support.

Figure 11:
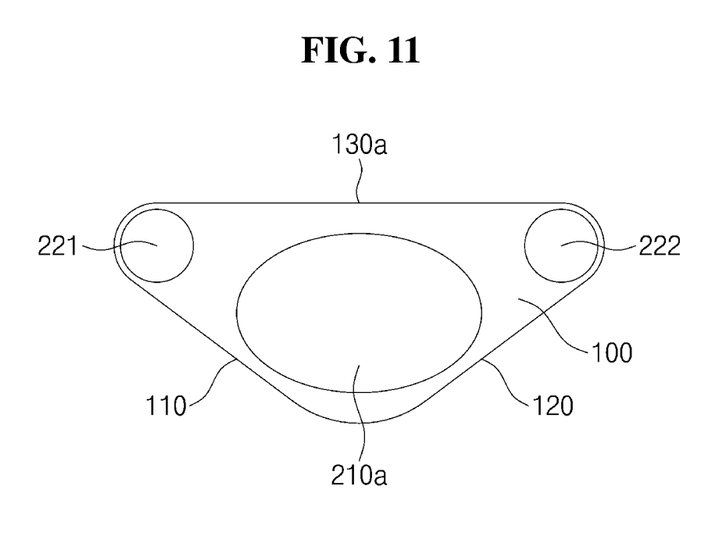
FIG. 11 is a plan view showing another embodiment of a main joint portion of an artificial spinal disc according to an embodiment of the present disclosure.

In a third embodiment, referring to FIG. 11, the upper disc 100 and the lower disc 300 have the third side 130a formed in a flat shape, the main joint portion 210a is formed in a semi-ellipsoidal shape, and the auxiliary joint portion 220 is formed in a hemispherical shape. In this instance, preferably, the main joint portion 210a is horizontally placed with the long axis of the ellipse facing the horizontal direction (the left-right direction of the spine) on the plane as shown.

Meanwhile, the foregoing description shows the upper disc 100 and the lower disc 300 configured with an approximate triangular shape as an embodiment. However, the upper disc 100 and the lower disc 300 may have curved sides, and the sides may be formed in a streamlined shape in the insertion direction.

A fourth embodiment will be described with reference to FIG. 12. The upper disc 100 and the lower disc 300 may be formed with the plane shape in a kidney bean shape including a first curved side 140 and a second curved side 150.

In detail, the first curved side 140 is formed along the anterior side of each of the first auxiliary joint portion 221a, the main joint portion 210 and the second auxiliary joint portion 222a and curves on the plane. The second curved side 150 is connected to the first curved side 140, and is formed along the posterior side of each of the first auxiliary joint portion 221a, the main joint portion 210a and the second auxiliary joint portion 222a and curves on the plane.

In the drawing, the first curved side 140 curves convexly, and the second curved side 150 curves concavely. However, this is an example, and both the first curved side 140 and the second curved side 150 may curve concavely to form a streamlined shape.

Here, the main joint portion 210a may be formed in a semi-ellipsoidal shape, and the first auxiliary joint portion 221a and the second auxiliary joint portion 222a may be also formed in a semi-ellipsoidal shape. In this instance, when the main joint portion 210a is formed in a semi-ellipsoidal shape, the main joint portion 210a is preferably positioned with the long axis of the ellipse facing the left-right direction on the plane, and the first auxiliary joint portion 221a and the second auxiliary joint portion 222a is preferably positioned with the long axis of the ellipse facing the front-rear direction on the plane.

Figure 12:
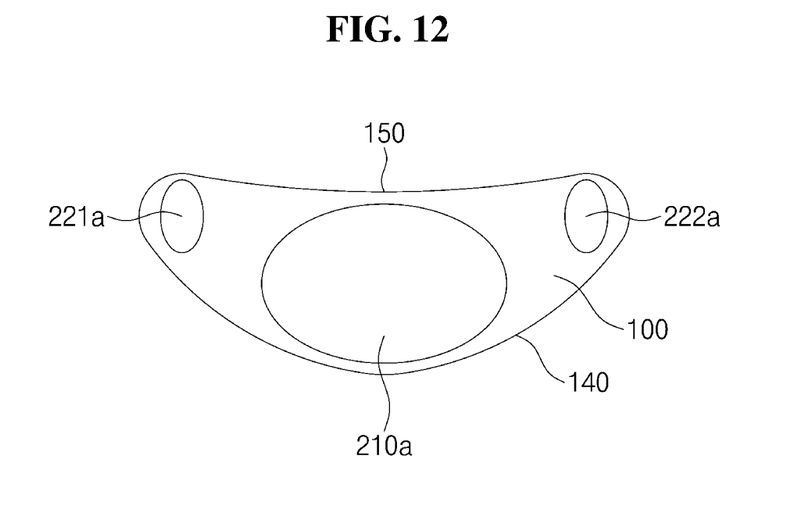
FIG. 12 is a plan view showing another embodiment of a main joint portion and an auxiliary joint portion having different shapes in an artificial spinal disc according to an embodiment of the present disclosure.
Figure 13:
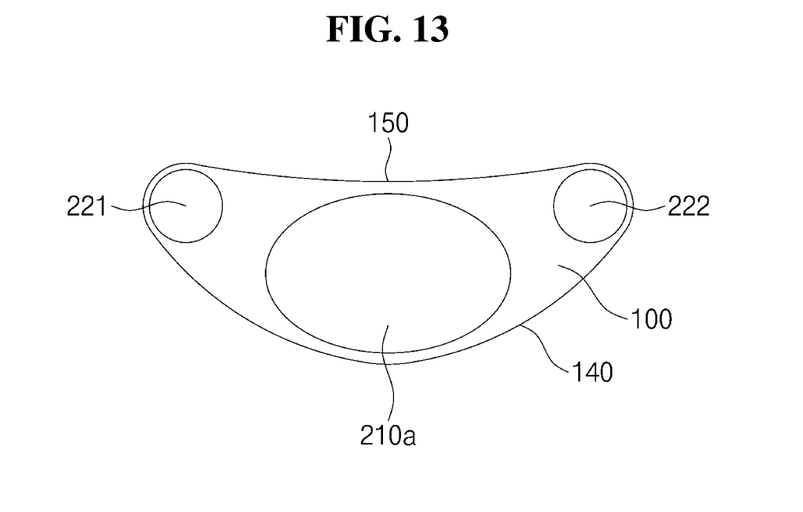
FIG. 13 is a plan view showing another embodiment of an upper disc and a lower disc having different side shapes in an artificial spinal disc according to an embodiment of the present disclosure.

In a fifth embodiment, referring to FIG. 13, compared to FIG. 12, the first auxiliary joint portion 221 and the second auxiliary joint portion 222 may be formed in a hemispherical shape. As described above, the main joint portion 210a, the first auxiliary joint portion 221 and the second auxiliary joint portion 222 may be formed in various shapes according to the surgery condition and the patient's condition.

Meanwhile, the present disclosure may have the same shape of the first auxiliary joint portion 221 and the second auxiliary joint portion 222 as the shape of the corresponding auxiliary joint groove 312 as described above, but as a different embodiment, the shape of the first auxiliary joint portion 221 and the second auxiliary joint portion 222 and the shape of the auxiliary joint groove 312a in contact with them may be different from each other. Describing with reference to FIG. 14, the first auxiliary joint portion 221 and the second auxiliary joint portion 222 may be formed in a hemispherical shape, and the corresponding auxiliary joint groove 312a may be formed in a semi-ellipsoidal shape.

Accordingly, the first auxiliary joint portion 221 and the second auxiliary joint portion 222 of a hemispherical shape may have the increased rotational movement in the auxiliary joint groove 312a of a semi-ellipsoidal shape, and through this, rotation between the upper disc 100 and the lower disc 300 increases, thereby allowing rotation in all the front-rear direction (x-axis rotation), left-right direction (y-axis rotation) and up-down direction (Z-axis rotation), and allowing for more diverse and flexible movements of the spine.

While the present disclosure has been hereinabove described with reference to the embodiments shown in the drawings, this is provided for illustration purposes only and it will be appreciated by those skilled in the art that various modifications and equivalents may be made thereto. Therefore, the true technical protection scope of the present disclosure should be defined by the technical spirit of the appended claims.

DETAILED DESCRIPTION OF MAIN ELEMENTS

| | |
|---|---|
| 100: Upper disc | 110, 110a, 310: First side |
| 111, 121, 131, 331: Concave portion | 120, 120a, 320: Second side |
| 130, 130a, 330: Third side | 140: First curved side |
| 150: Second curved side | 200: Protruding joint portion |
| 210: Main joint portion | 220: Auxiliary joint portion |
| 221: First auxiliary joint portion | 222: Second auxiliary joint portion |
| 300: Lower disc | 311: Main joint groove |
| 312: Auxiliary joint groove | 500: Artificial disc |

The invention claimed is:

1. An artificial spinal disc configured to be inserted between an upper vertebra and a lower vertebra of a spine, the artificial spinal disc comprising:
   an upper disc having an approximate triangular plane shape having a first side, a second side, and a third side;
   a main joint portion spaced apart from a first auxiliary joint portion and a second auxiliary joint portion, wherein the main joint portion, the first auxiliary joint portion, and the second auxiliary joint portion protrude from a lower surface of the upper disc; and
   a lower disc having an approximate triangular plane shape, wherein the lower disc has, on an upper surface thereof, a main joint groove in which the main joint portion is seated, a first auxiliary joint groove in which the first auxiliary joint portion is seated, and a second auxiliary joint groove in which the second auxiliary joint portion is seated to allow the main joint portion, the first auxiliary joint portion and the second auxiliary joint portion to make multidirectional movements,
   wherein the approximate triangular plane shape of the lower disc has a first side, a second side, and a third side,
   wherein the first side of the upper disc is parallel to the first side of the lower disc, the second side of the upper disc is parallel to the second side of the lower disc, and the third side of the upper disc is parallel to the third side of the lower disc,
   wherein the first auxiliary joint portion and the second auxiliary joint portion are symmetrically disposed with respect to the main joint portion on the approximate triangular plane shape of the upper disc,
   wherein a center of each of the first auxiliary joint portion and the second auxiliary joint portion are configured to be disposed at an anterior side of the spine with respect to a center of the main joint portion,
   wherein the first side of the upper and lower discs and the second side of the upper and lower discs are configured to be disposed between the anterior side of the spine and the posterior side of the spine;
   wherein the third side of the upper disc has at least two concave portions and the third side of the lower disc has at least two concave portions,
   wherein the third side of the upper disc and the third side of the lower disc are configured to be disposed at the anterior side of the spine, and
   wherein the main joint portion is disposed adjacent to a first vertex of the approximate triangular plane shape of the upper disc, the first vertex connects the first side of the upper disc to the second side of the upper disc, the first auxiliary joint portion is disposed adjacent to a second vertex of the approximate triangular plane shape of the upper disc, and the second auxiliary joint portion is disposed adjacent to a third vertex of the approximate triangular plane shape of the upper disc.

2. The artificial spinal disc according to claim 1, wherein the main joint portion has a protrusion height which is higher than a protrusion height of the first auxiliary joint portion and a protrusion height of the second auxiliary joint portion.

3. The artificial spinal disc according to claim 1, wherein each of the first auxiliary joint portion and the second auxiliary joint portion has a hemispherical shape.

4. The artificial spinal disc according to claim 1, wherein the main joint portion has a hemispherical shape.

5. The artificial spinal disc according to claim 1, wherein the main joint portion, the first auxiliary joint portion, and the second auxiliary joint portion are integrally formed with the upper disc.

6. The artificial spinal disc according to claim 1, wherein the upper disc and the lower disc are spaced apart from each other at a distance between the lower surface of the upper disc and the upper surface of the lower disc in a range of 3 mm to 6 mm when the main joint portion is seated on the main joint groove, the first auxiliary joint portion is seated on the first auxiliary joint groove, and the second auxiliary joint portion is seated on the second auxiliary joint groove.

7. The artificial spinal disc according to claim 1, wherein the first auxiliary joint portion and the second auxiliary joint portion have a smaller planar area than a planar area of the main joint portion.

8. The artificial spinal disc according to claim 1, wherein the first auxiliary joint portion and the second auxiliary joint portion have a same shape and planar area.

9. An artificial spinal disc configured to be inserted between an upper vertebra and a lower vertebra of a spine, the artificial spinal disc comprising:
   an upper disc having an approximate triangular plane shape having a first side, a second side, and a third side;
   a main joint portion spaced apart from a first auxiliary joint portion and a second auxiliary joint portion, wherein the main joint portion, the first auxiliary joint portion, and the second auxiliary joint portion protrude from a lower surface of the upper disc; and
   a lower disc having an approximate triangular plane shape, wherein the lower disc has, on an upper surface thereof, a main joint groove in which the main joint portion is seated, a first auxiliary joint groove in which the first auxiliary joint portion is seated, and a second auxiliary joint groove in which the second auxiliary joint portion is seated to allow the main joint portion, the first auxiliary joint portion and the second auxiliary joint portion to make multidirectional movements,
   wherein the approximate triangular plane shape of the lower disc has a first side, a second side, and a third side,
   wherein the first side of the upper disc is parallel to the first side of the lower disc, the second side of the upper disc is parallel to the second side of the lower disc, and the third side of the upper disc is parallel to the third side of the lower disc;
   wherein the third side of the upper disc has at least two concave portions and the third side of the lower disc has at least two concave portions,
   wherein the main joint portion is disposed adjacent to a first vertex of the approximate triangular plane shape of the upper disc, the first vertex connects the first side of the upper disc to the second side of the upper disc, the first auxiliary joint portion is disposed adjacent to a second vertex of the approximate triangular plane shape of the upper disc, and the second auxiliary joint portion is disposed adjacent to a third vertex of the approximate triangular plane shape of the upper disc,
   wherein the main joint groove has a corresponding same shape of the main joint portion, and the auxiliary joint groove has a corresponding same shape of the auxiliary joint portion, and
   wherein the main joint portion has a protrusion height which is higher than a protrusion height of the first auxiliary joint portion and a protrusion height of the second auxiliary joint portion.

10. The artificial spinal disc according to claim 9, wherein the first auxiliary joint portion and the second auxiliary joint portion are symmetrically disposed with respect to the main joint portion on the approximate triangular plane shape.

11. The artificial spinal disc according to claim 9, wherein a center of each of the first auxiliary joint portion and the second auxiliary joint portion is disposed at an anterior side of the spine with respect to a center of the main joint portion.

12. The artificial spinal disc according to claim 9, wherein the third side of the upper and lower discs is disposed at an anterior side of the spine.

13. The artificial spinal disc according to claim 9, wherein each of the first auxiliary joint portion and the second auxiliary joint portion has a hemispherical shape.

14. The artificial spinal disc according to claim 9, wherein the main joint portion has a hemispherical shape.

15. The artificial spinal disc according to claim 9, wherein the main joint portion, the first auxiliary joint portion, and the second auxiliary joint portion are integrally formed with the upper disc.

16. The artificial spinal disc according to claim 9, wherein the upper disc and the lower disc are spaced apart from each other at a distance between the lower surface of the upper disc and the upper surface of the lower disc in a range of 3 mm to 6 mm the main joint portion is seated on the main joint groove, the first auxiliary joint portion is seated on the first auxiliary joint groove, and the second auxiliary joint portion is seated on the second auxiliary joint groove.

17. The artificial spinal disc according to claim 9, wherein the first auxiliary joint portion and the second auxiliary joint portion have a smaller planar area than a planar area of the main joint portion.

18. The artificial spinal disc according to claim 9, wherein the first auxiliary joint portion and the second auxiliary joint portion have a same shape and planar area.

* * * * *